United States Patent [19]

Crosbie

[11] Patent Number: 5,266,112
[45] Date of Patent: Nov. 30, 1993

[54] PORTABLE LATENT FINGERPRINT FUMING APPARATUS

[76] Inventor: David B. Crosbie, 13228 Highview Dr., Burnsville, Minn. 55337

[21] Appl. No.: 29,907

[22] Filed: Mar. 11, 1993

[51] Int. Cl.⁵ ............................................. A61B 5/117
[52] U.S. Cl. ................................... 118/31.5; 118/728; 118/733; 118/50; 427/1; 401/9
[58] Field of Search ................ 118/31.5, 50, 715, 728, 118/733; 427/1; 401/11, 192, 9

[56] References Cited

U.S. PATENT DOCUMENTS

| | | | |
|---|---|---|---|
| 2,496,054 | 1/1950 | Hoyler | 118/733 |
| 4,297,383 | 10/1981 | Bourdon | 118/31.5 |
| 4,504,408 | 3/1985 | Morton | 118/31.5 |
| 4,700,657 | 10/1987 | Butland | 118/31.5 |
| 4,806,380 | 2/1989 | Sato et al. | 118/31.5 |

OTHER PUBLICATIONS

*Crime Scene Investigator's Catalog.* Lynn Peavey Company, 1991 catalog.
*Lightning Powder Company, Inc.* Catalog, Jan. 1992.
"Advantages of Glue Fuming", 4 *Minutiae.* Jul.-Aug. 1992.

*Primary Examiner*—W. Gary Jones
*Assistant Examiner*—Todd J. Burns
*Attorney, Agent, or Firm*—Palmatier, Sjoquist & Helget

[57] ABSTRACT

A portable latent fingerprint fuming apparatus for developing white-colored crystallized prints on nonporous, flat and uneven surfaces as well as objects has an air-tight housing. The housing has a sidewall, a ceiling, an aperture through the housing and an open bottom with an expansible, pliable boot or flange therearound extending downwardly and having a lowermost pliable flange adapted to air-tight sealably engage the nonporous, flat and uneven surfaces. A receptacle may be provided for holding super glue or cyanoacrylate within the housing. A vacuum pump is in flow communication with the aperture, suitably by tubing, for vacuuming air out of the housing sealably engaged with the nonporous surface, for creating negative pressure within the housing and about the latent fingerprint, and for vaporizing the cyanoacrylate for deposition upon, and crystallization of, the ridges of the latent fingerprint.

17 Claims, 2 Drawing Sheets

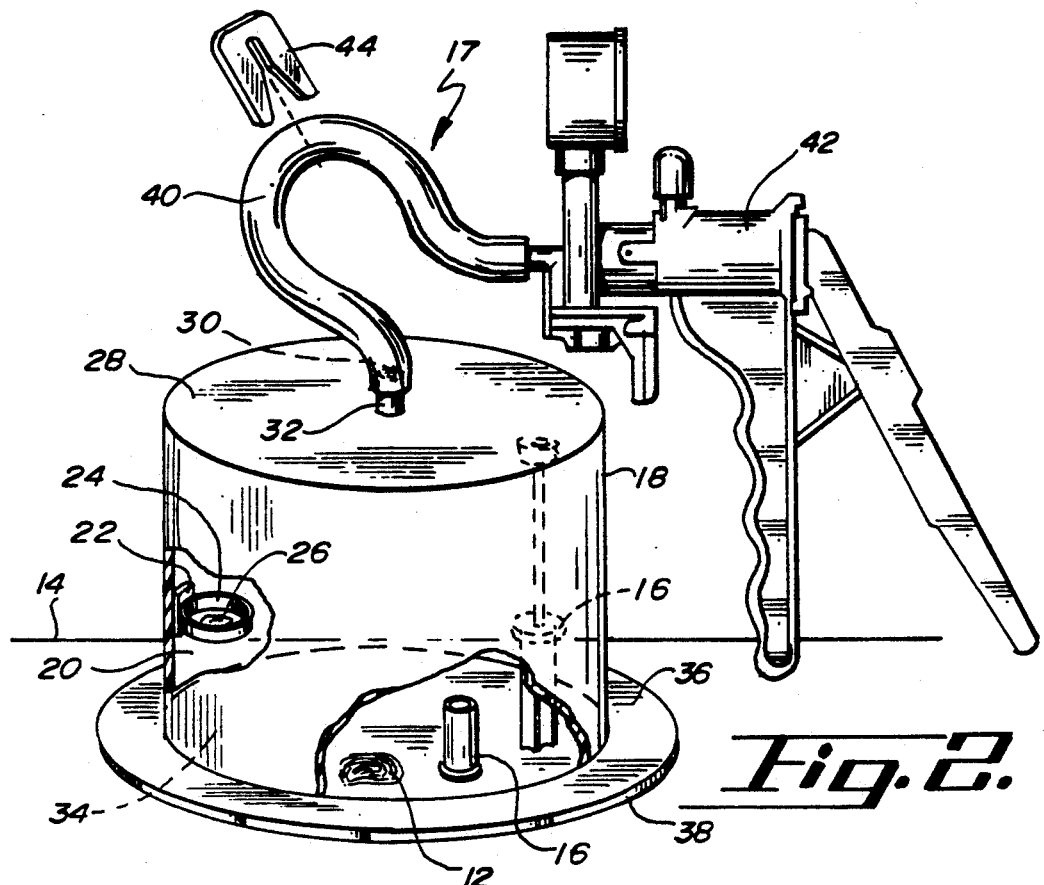
Fig. 2.
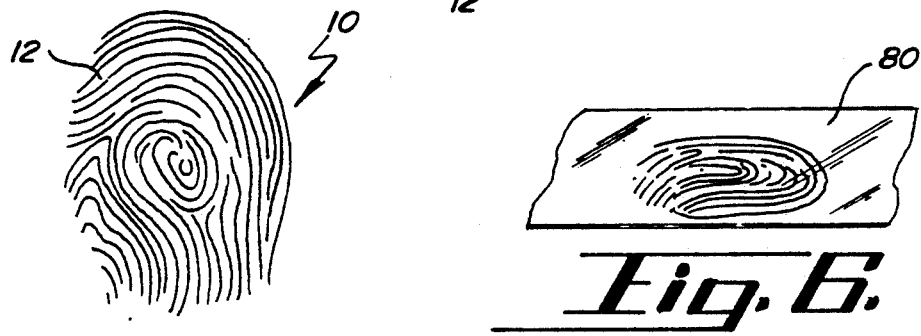
Fig. 1.
Fig. 6.
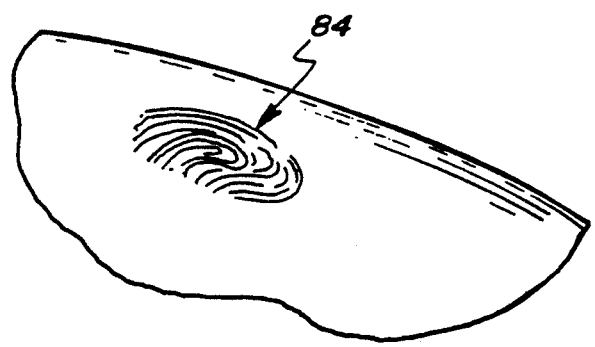
Fig. 5.

PORTABLE LATENT FINGERPRINT FUMING APPARATUS

BACKGROUND OF THE INVENTION

The present invention relates to crime scene evidence, and more particularly, to a portable latent fingerprint fuming apparatus for developing white-colored crystallized fingerprints.

It is well known that human beings each have their own individualized fingerprints. It may well be said that no two fingerprints are alike. Consequently, whenever someone leaves their fingerprints behind at a crime scene, a suspect may be identified who has the same fingerprints.

Over the years, forensic technology permitted law enforcement technicians to effectively dust fingerprints and remove the dusted print from a particular surface or object with a clear tape. Fingerprints permit and attract dusting due to their ridges of residue, including oils, amino acids, moisture and fats. However, with dusting and taping, fingerprints can typically only be taken once and are highly susceptible to being damaged prior to fixation.

Consequently, forensic research over the years has developed glue fuming which is a chemical step recommended for almost all latent print processing techniques for nonporous objects or items. The item or object to be fumed is subjected to cyanoacrylate, which is commonly or generically termed super glue.

The cyanoacrylate or super glue is a quick bonding material that is further characterized by having an odoriferous eye and nose irritating vapor or toxic fume that reacts with trace amounts of latent fingerprint residues to develop a white-colored, hard, "petrified" print impression suitable for multiple powdering and lifting off with a tape or otherwise photographed.

Due to the harmful nature of the cyanoacrylate or super glue, glue fuming is most often conducted in an enclosed container, such as an aquarium or an enclosed plexiglass box. A cup of warm water is added to the inside of the aquarium to add humidity to the chamber to enhance crystallization of the latent print. A few drops of the liquid super glue are placed in a small dish or on a piece of aluminum foil within the aquarium. Thereafter the aquarium or container is closed for fuming which may take ten to fifteen minutes or longer depending on the humidity and the ambient temperature.

Fuming by this passive aquarium or container process is subject to a variety of problems. Too much fuming of the latent fingerprint will cover the entire surface of the item with a white residue and the ridges of the latent prints may actually be filled in. Over-fumed prints are difficult if not impossible to save because subsequent dusting or dye staining will adhere to the entire surface of the object or surface, obscuring the ridge detail. This mishap could easily occur when the technician is called away or forgets about the evidence in the fuming cabinet. Additionally, many objects, such as wadded up plastic materials or bags are difficult to be fumed because of the multiplicity of convolutions causing the inability to expose all surfaces to the vaporizing super glue. Large surfaces also do not lend themselves to fuming as they will not fit in fuming tanks. Also, fuming in tanks or aquariums often necessitates solvent cleaning of the fuming container making for an additional mess and further harmful vapors.

Recently, vacuum systems, that are very expensive and quite large, have been developed which make it next to impossible to over-fume objects and items placable within the fuming container. Also, there is no buildup of white residue on the inside of the fuming chamber or container. Additionally, glue fumes reach all sides and surfaces of the fumed object, whether crumpled or wadded, within the fuming chamber. Fuming by this method is typically accomplished by evacuating the chamber down to twenty-five inches of mercury and allowing the items to fume under vacuum for about twenty minutes. Thereafter, the latent prints are "locked on" the item for future print removal and study.

There is a need for a portable latent fingerprint fuming apparatus that will not only fume items and objects but even, uneven and curved nonporous surfaces without the need for expensive, large and complex vacuum systems.

SUMMARY OF THE INVENTION

A portable latent fingerprint fuming apparatus for developing white-colored crystallized prints on nonporous, flat and uneven surfaces as well as objects has an air-tight housing. The housing has a sidewall, a ceiling, an aperture through the housing and an open bottom with an expansible, pliable boot or flange therearound extending downwardly and having a lowermost pliable flange adapted to air-tight sealably engage the nonporous, flat and uneven surfaces. A receptacle may be provided for holding super glue or cyanoacrylate within the housing. A vacuum pump is in flow communication with the aperture, suitably by tubing, for vacuuming air out of the housing sealably engaged with the nonporous surface, for creating negative pressure within the housing and about the latent fingerprint, and for vaporizing the cyanoacrylate for deposition upon, and crystallization of, the ridges of the latent fingerprint.

A principal object and advantage of the present invention relates to its portability, simplicity and inexpensive construction.

Another object and advantage of the present apparatus is that it requires no electricity, permitting the fuming of latent fingerprints almost anywhere without electrical power.

Another object and advantage of the present invention is that it permits fuming of more than just objects and items, but also substantially large, flat, curved, uneven, nonporous surfaces which otherwise would not fit within vacuum systems of the past.

Another object and advantage of the present invention is that the fuming of objects as well as surfaces is easily accomplished with the present invention without the removal or touching of the object or item to be fumed so long as it remains on a nonporous surface over which the housing may be fitted.

Another object and advantage of the present simple and inexpensive invention is that all of the advantages of the complex, expensive vacuum systems are present, including the absence of over-fuming and ability to fume crumpled objects.

Other objects and advantages will become apparent upon review of the accompanying figures, following specification and appended claims.

BRIEF DESCRIPTION OF THE DRAWINGS

FIG. 1 is a top plan view of a latent fingerprint showing the ridges;

FIG. 2 is a side elevational view of the apparatus on a nonporous, even surface with the housing partially broken away to expose the glue receptacle, surface fingerprint and objects therein for fuming;

FIG. 5 is a perspective view of a crystallized fumed print on an uneven surface ready for application of a dye or dusting; and FIG. 6 is a front elevational view of a taped fingerprint removed from the crystallized print after being treated with a dye or dust.

DETAILED SPECIFICATION

Referring to FIG. 1, a latent finger print 10 may be seen. The print is comprised of an individual matrix of ridges 12 comprised of oils, moisture, fats and amino acids residues readily susceptible to crystallization by glue fuming with cyanoacrylate.

Figure 3:
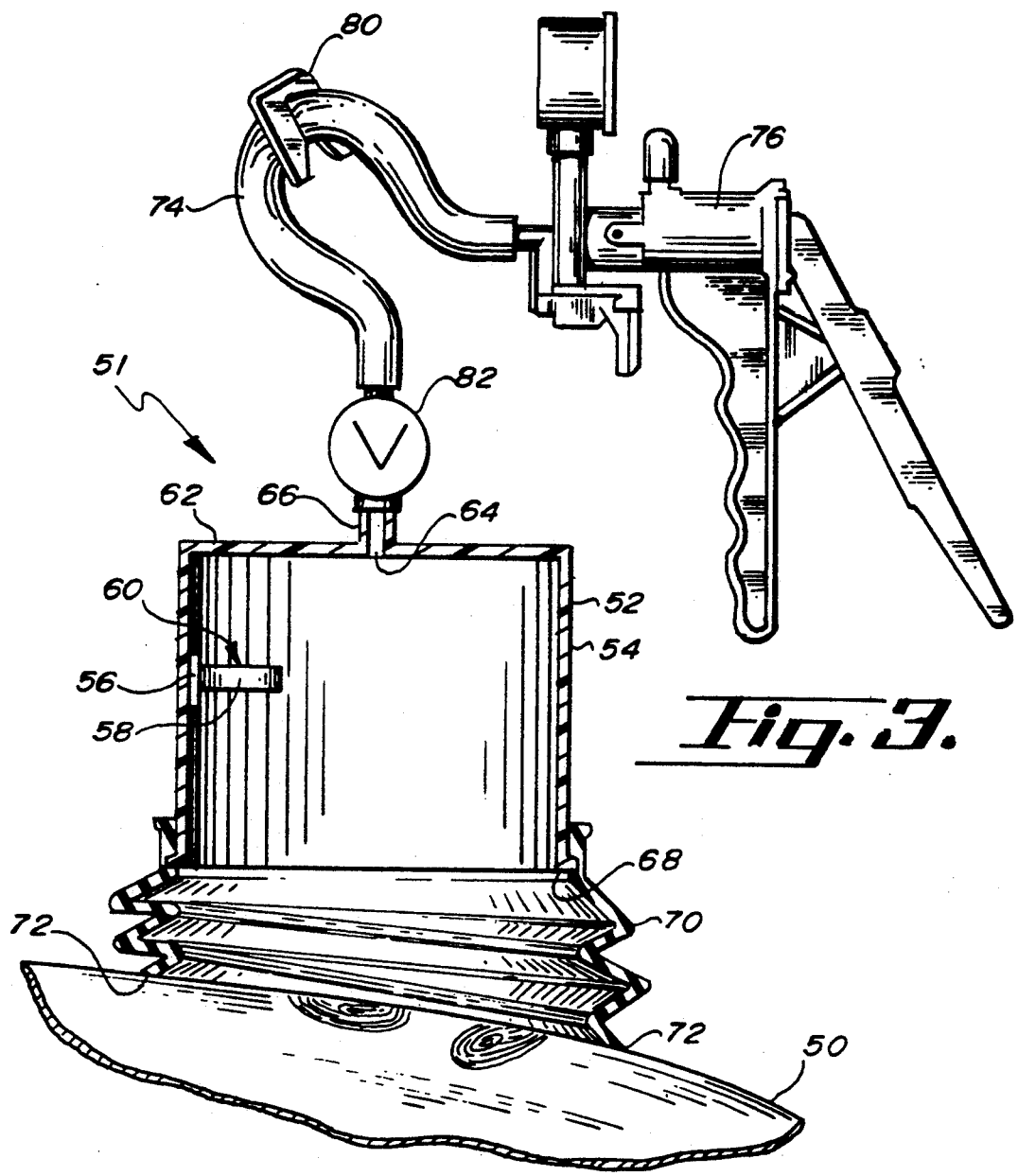
FIG. 3 is an alternate embodiment of the apparatus which is readily adaptable for air tight sealing on nonporous, uneven surfaces.
Figure 4:
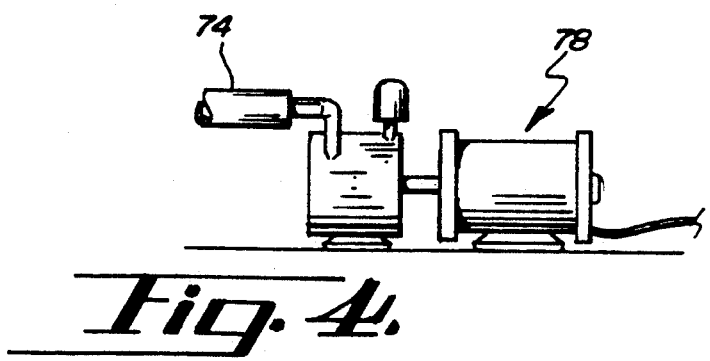
FIG. 4 is a side elevational view of an electric vacuum pump which optionally may be used with the present invention.

Referring generally to FIGS. 2 and 3, the portable, latent fingerprint fuming apparatus 17 may generally be seen. The apparatus 17 includes a housing 18 suitably of a clear plastic or plexiglass to permit viewing within the housing. The housing 18 has a sidewall 20 therearound with a magnet 22 suitably glued to the sidewall 20. Magnet 22 permits the support of a metal cup 24 along the sidewall 20 in various orientations which will receive the super glue or cyanoacrylate 26. The housing 18 has a ceiling 28 with an aperture 30 therethrough whereat is located a nipple 32. Housing 18 has an open bottom 34 appropriately with a flange 36 therearound having a silicone, urethane or elastomer seal 38 sealably engagable with a flat surface 14. A vinyl tube 40 extends from the aperture 32 in flow communication with the interior of housing 18. Suitably a hand-operated vacuum pump 42 will remove air from the sealed housing 18 down to 25 inches of mercury. A suitable hand-operated vacuum pump is marketed under the trademark MITYVAC II ® by Neward Enterprises, Inc. of Cucamonga, California. FIG. 4 shows that a small electrical vacuum pump and motor combination, as is commonly available, will readily work and connect with vinyl tube 40. A constriction clamp 44 in the form of a notched piece of plastic or metal, a hemostat, or a crimp clamp 44 may be used for sealing the interior housing 18 to prevent the loss of vacuum after the vacuum pump 42 is turned off or stopped and suitably removed from vinyl tube 40 for operation and use with the next apparatus to fume prints at a different locale.

Referring to FIG. 2, a non porous, uneven surface 50 may be seen wherein the portable latent fingerprint fuming apparatus 51 of the present invention may be utilized. The apparatus 51 includes a housing 52, sidewall 54, magnet 56 attached to sidewall which supports a metal cup 58 and receives the glue 60 therein. The housing 52 also has a ceiling 62 with an aperture 64 therethrough whereat nipple 66 is located. Housing 52 also has an open bottom 68. Around the open bottom 68 suitably is affixed a pleated, expansible boot or bellows which extends downwardly and has a lowermost pliable flange 72 engagable with any of a variety of uneven and nonporous surfaces 50.

Vinyl tube 74 may extend from nipple 66 or it may be readily adaptable to fitted with a valve 82 (schematically shown) which permits the closure of nipple 66 to retain the vacuum within the housing 52. Alternatively, vinyl tube 74 may be connected to a hand-operated vacuum pump 76 or the previously disclosed electrical pump 78. Suitably a constriction clamp 80 may also be used.

Referring to FIGS. 5 and 6, the petrified, crystallized print 84 may be seen. The print is initially dusted or dyed afterwhich a tape 86 may be placed over the print and removed for preservation of the print. This process may be repeated several times as is needed.

The present invention may be embodied in other specific forms without departing from the spirit of essential attributes thereof; therefore, the illustrated embodiment should be considered in all respects as illustrative and not restrictive, reference being made to the appended claims rather than to the foregoing description to indicate the scope of the invention.

I claim:

1. A portable latent fingerprint fuming apparatus for developing white-colored crystallized prints on nonporous surfaces and objects having latent fingerprints thereon with ridges of residues, including oils, amino acids, moisture and fats, the apparatus comprising:
   (a) an air-tight housing having a sidewall, a ceiling, an aperture through the housing, an open bottom with a pliable flange extending around the open bottom adapted to air-tight sealably engage the nonporous surface and a portion of cyanoacrylate within the housing; and
   (b) a vacuum pump in flow communication with the aperture for vacuuming air out of the housing sealably engaged with the nonporous surface, for creating negative pressure within the housing and about the latent fingerprint, and for vaporizing the cyanoacrylate for deposition upon and crystallization of the ridges of the latent fingerprint.

2. The fuming apparatus of claim 1, wherein the vacuum pump is hand-actuated.

3. The fuming apparatus of claim 1, wherein the vacuum pump is electric.

4. The fuming apparatus of claim 1, further comprising a hollow constrictable tube in flow communication between the pump and the aperture.

5. The fuming apparatus of claim 4, further comprising a constriction clamp securable about the tube to maintain the vacuum within the housing when vacuum pump is not in operation and when the tube is removed from the pump.

6. The fuming apparatus of claim 1, wherein the housing is made of a clear plastic.

7. The fuming apparatus of claim 1, further comprising a magnet affixed to the inner wall for releasably holding a metal container in an upright condition despite the orientation of the housing, said metal container receiving the cyanoacrylate therein.

8. The fuming apparatus of claim 1 further comprising a pleated expansible boot around and extending downwardly from the open bottom and having the pliable flange on the bottom of the boot for fitting of the housing to nonporous uneven surfaces.

9. The fuming apparatus of claim 1, further comprising a valve in-line between the aperture and the pump.

10. A portable latent fingerprint fuming apparatus for developing white-colored crystallized prints on nonporous, flat and uneven surfaces and objects having latent fingerprints thereon with ridges of residues, including oils, amino acids, moisture and fats, the apparatus comprising:
 (a) an air-tight housing having a sidewall, a ceiling, an aperture through the housing, an open bottom with a pleated expansible bellows-like boot therearound and extending downwardly having a lowermost pliable flange adapted to air-tight sealably engage the nonporous, flat and uneven surfaces, and a portion of cyanoacrylate within the housing; and
 (b) a vacuum pump in flow communication with the aperture for vacuuming air out of the housing sealably engaged with the nonporous surface, for creating negative pressure within the housing and about the latent fingerprint, and for vaporizing the cyanoacrylate for deposition upon and crystallization of the ridges of the latent fingerprint.

11. The fuming apparatus of claim 10 wherein the vacuum pump is hand-actuated.

12. The fuming apparatus of claim 10, wherein the vacuum pump is electric.

13. The fuming apparatus of claim 10, further comprising a hollow constrictable tube in flow communication between the pump and the aperture.

14. The fuming apparatus of claim 13, further comprising a constriction clamp securable about the tube to maintain the vacuum within the housing when vacuum pump is not in operation and when the tube is removed from the pump.

15. The fuming apparatus of claim 10, wherein the housing is made of a clear plastic.

16. The fuming apparatus of claim 10, further comprising a magnet affixed to the inner wall for releasably holding a metal container in an upright condition despite the orientation of the housing, said metal container for receiving the cyanoacrylate therein.

17. A portable latent fingerprint fuming apparatus for developing white-colored crystallized prints on nonporous, flat and uneven surfaces and objects having latent fingerprints thereon with ridges of residues, including oils, amino acids, moisture and fats, the apparatus comprising:
 (a) an air-tight housing having a sidewall, a ceiling, an aperture through the housing with a hollow tube extending therefrom, an open bottom with a pleated expansible bellows-like boot therearound and extending downwardly having a lowermost pliable flange adapted to air-tight sealably engage the nonporous, flat and uneven surfaces, and a portion of cyanoacrylate within the housing;
 (b) a hand-actuated vacuum pump connected to the tube in flow communication with the aperture for vacuuming air out of the housing sealably engaged with the nonporous surface, for creating negative pressure within the housing and about the latent fingerprint and for vaporizing the cyanoacrylate for deposition upon and crystallization of the ridges of the latent fingerprint; and
 (c) constricting means for closing the tube for maintaining a vacuum within the housing.

* * * * *

UNITED STATES PATENT AND TRADEMARK OFFICE
CERTIFICATE OF CORRECTION

PATENT NO. : 5,266,112

DATED : November 30, 1993

INVENTOR(S) : David B. Crosbie

It is certified that error appears in the above-identified patent and that said Letters Patent is hereby corrected as shown below:

In column 4, line 33, after "surface", please insert --,-- (a comma).

In column 6, line 7, please delete the word "for".

Signed and Sealed this

Seventeenth Day of May, 1994

*Attest:*

BRUCE LEHMAN

*Attesting Officer*    *Commissioner of Patents and Trademarks*